(12) United States Patent
Tu et al.

(10) Patent No.: US 10,961,194 B2
(45) Date of Patent: Mar. 30, 2021

(54) METHOD FOR PURIFYING ROPINIROLE HYDROCHLORIDE

(71) Applicants: Zhejiang Huahai LiCheng Pharmaceutical Co., Ltd., Taizhou (CN); Zhejiang Huahai Pharmaceutical Co., Ltd., Taizhou (CN)

(72) Inventors: Guoliang Tu, Linhai (CN); Zhongming Xu, Linhai (CN); Tao Zhou, Linhai (CN); Wenfeng Huang, Linhai (CN); Shiwen Zhang, Linhai (CN)

(73) Assignees: ZHEJIANG HUAHAI LICHENG PHARMACEUTICAL CO., LTD., Linhai (CN); ZHEJIANG HUAHAI PHARMACEUTICALS CO., LTD., Linhai (CN)

( * ) Notice: Subject to any disclaimer, the term of this patent is extended or adjusted under 35 U.S.C. 154(b) by 0 days.

(21) Appl. No.: 16/623,085

(22) PCT Filed: Jun. 16, 2017

(86) PCT No.: PCT/CN2017/088651
§ 371 (c)(1),
(2) Date: Dec. 16, 2019

(87) PCT Pub. No.: WO2018/227553
PCT Pub. Date: Dec. 20, 2018

(65) Prior Publication Data
US 2020/0172482 A1 Jun. 4, 2020

(51) Int. Cl.
*C07D 209/34* (2006.01)
(52) U.S. Cl.
CPC ................... *C07D 209/34* (2013.01)

(58) Field of Classification Search
CPC .................................................. C07D 209/34
See application file for complete search history.

(56) References Cited

U.S. PATENT DOCUMENTS

| 4,452,808 | A | 6/1984 | Gallagher, Jr. |
| 4,997,954 | A | 3/1991 | Fortunak |
| 2005/0159605 | A1 | 7/2005 | Tarur et al. |
| 2007/0032540 | A1 | 2/2007 | Bosch Cartés et al. |
| 2007/0254941 | A1 | 11/2007 | Kumar et al. |

FOREIGN PATENT DOCUMENTS

| CN | 1909901 A | 2/2007 |
| EP | 0 300 614 A1 | 1/1969 |
| WO | WO 94/15918 | 7/1994 |
| WO | WO 2005/067922 A1 | 7/2005 |
| WO | WO 2011/072704 A1 | 6/2011 |

*Primary Examiner* — Shawquia Jackson
(74) *Attorney, Agent, or Firm* — Blank Rome LLP

(57) ABSTRACT

Provided is a method for purifying ropinirole hydrochloride (4-2-di-n-propylaminoethyl-1,3-dihydro-2H-indole-2-keto-hydrochloride). The method comprises: adding ropinirole hydrochloride containing a monopropyl impurity A into water, adding organic solvent, stirring and dissolving at room temperature, adding alkali, stirring, standing, demixing, and removing an aqueous layer; optionally, drying the organic layer by using anhydrous magnesium sulfate, and filtering; and adding acyl chloride or acid anhydride into the organic layer, stirring, concentrating the organic layer to be dry, adding an organic solvent into the obtained oily matter, adding concentrated hydrochloric acid, and stirring, so as to obtain the ropinirole hydrochloride. By using the method, the impurity A in the ropinirole hydrochloride can be effectively removed, and the ropinirole hydrochloride can be obtained with a high yield and a high purity, so that the impurity A is controlled and the purity of the product reaches a medicinal standard.

20 Claims, No Drawings

METHOD FOR PURIFYING ROPINIROLE HYDROCHLORIDE

RELATED APPLICATIONS

This application is a national phase application of PCT/CN2017/088651, filed Jun. 16, 2017. The entire content of this application is incorporated herein by reference.

FIELD OF THE INVENTION

The present invention relates to a method for purifying ropinirole hydrochloride, and in particular to a method for purifying ropinirole hydrochloride by removing impurity A monopropyl ropinirole. The impurity A has a structural formula (I):

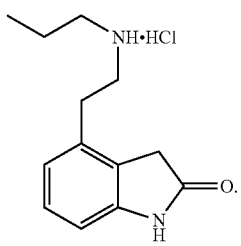

BACKGROUND OF THE INVENTION

Ropinirole hydrochloride was developed by GlaxoSmithKline (GSK) and was the first generic drug of ropinirole hydrochloride approved by the US Food and Drug Administration (FDA).

Ropinirole hydrochloride is used to treat moderate to severe restless legs syndrome (RLS). In addition to this, FDA has approved ropinirole hydrochloride for the treatment of Parkinson's disease. The generic drug of ropinirole hydrochloride can only be approved for the treatment of the restless legs syndrome, because the use of ropinirole hydrochloride for the treatment of Parkinson's disease is patented. Once the use patent of ropinirole hydrochloride for the treatment of Parkinson's disease filed by the original drug company is expired, it is possible for the generic drug manufacturer to seek for approval of use of the drug for the treatment of Parkinson's disease. The structural formula of ropinirole hydrochloride is as shown in the following formula (II):

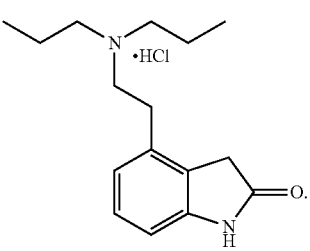

At present, there are mainly five methods for preparing ropinirole hydrochloride reported in the patent or non-patent literatures, and they respectively use 2-methyl-3-nitro-benzoic acid as raw material (U.S. Pat. No. 4,452,808), 3-bromoethylaniline (WO1994/015918) as raw material, isochroman as raw material (EP0300614 and U.S. Pat. No. 4,997,954), 4-indole formaldehyde as raw material (US2007032540), and o-bromoethylbenzaldehyde as raw material (US0156505) to synthesize ropinirole hydrochloride.

Specifically, in the U.S. Pat. No. 4,452,808, 2-methyl-3-nitro-benzoic acid was used as raw material, then subjected to a borane hydrogenation reaction, followed by addition of thionyl chloride to obtain acyl chloride, followed by cyanation and hydrolysis to obtain 2-methyl-3-nitro-phenylacetic acid and then to prepare amide, and followed by hydrogenation reduction, condensation, oxidative hydrolysis, a final hydrogenation reduction and salt formation to obtain ropinirole hydrochloride. In the patent application WO1994/015918, 3-bromoethylaniline was used as raw material, and subjected to cyclization, oxidation, substitution, and reduction to obtain ropinirole hydrochloride. In the patents EP0300614 and U.S. Pat. No. 4,997,954, isochroman was used as raw material, and subjected to bromination and ring opening reaction so as to produce a nitrostyrene compound under the effect of a strong alkali, followed by ring closure reaction, reduction and substitution reaction to obtain ropinirole hydrochloride. In the patent US2007032540, 4-indole formaldehyde was used as raw material, and subjected to a reaction with nitromethane to obtain a nitrostyrene compound, followed by hydrogenation reduction, addition with propionic acid, reduction and a final oxidation to obtain ropinirole hydrochloride. Finally, in the patent US0156505, o-bromoethylbenzaldehyde was used as a raw material, and subjected to substitution and a reaction with nitromethane to produce a nitrostyrene compound, followed by cyclization, oxidation, hydrolysis, and the like to obtain ropinirole hydrochloride.

However, none of the above documents refers to an important problem in production, that is, in the one-step intermediate for preparing ropinirole hydrochloride, a monopropyl impurity by-product is generated due to excessive oxidization, and the impurity is converted into ropinirole hydrochloride impurity A, i.e. monopropyl ropinirole in the last step. The impurity is produced in many synthetic routes. In particular, in the U.S. Pat. No. 4,452,808, the impurity A is a by-product contained in the intermediate for preparing ropinirole hydrochloride, and ropinirole hydrochloride containing the impurity A is obtained after hydrogenation reduction and salt formation. It is very difficult to separate the impurity A from the ropinirole hydrochloride product by conventional means due to their similar structure. Routine methods such as solvent washing, slurrying, recrystallization and the like are very difficult to remove the impurity A, and meanwhile will further affect the yield of ropinirole hydrochloride product. Therefore, there is a need for a simple, inexpensive, and efficient purification process to remove the impurity A.

SUMMARY OF THE INVENTION

The inventors have developed a method for purifying ropinirole hydrochloride, 4-(2-di-n-propylaminoethyl)-1,3-dihydro-2H-indol-2-one hydrochloride, which is simple, inexpensive and efficient to remove the impurity A (structural formula I).

Specifically, the present invention provides a method for purifying ropinirole hydrochloride, 4-(2-di-n-propylaminoethyl)-1,3-dihydro-2H-indol-2-one hydrochloride, represented by structural formula (II), comprising the following steps:

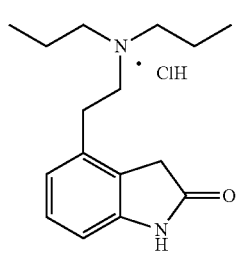

Ropinirole hydrochloride (II)

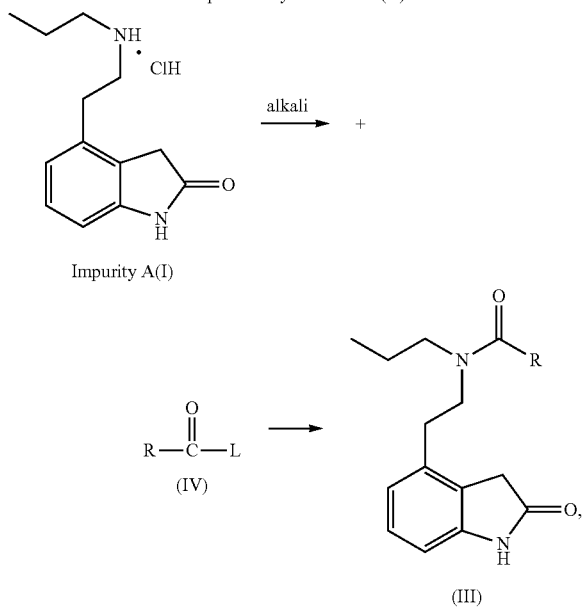

Impurity A(I)

(IV)

(III)

wherein —R represents $C_1$-$C_6$ alkyl or a $C_6$-$C_{10}$ aromatic group; -L represents halogen —X, or acyloxy

wherein halogen is fluorine, chlorine, bromine or iodine;

(1) mixing ropinirole hydrochloride containing an impurity A monopropyl ropinirole represented by a structural formula (I) with water and an organic solvent, stirring and dissolving to obtain a clear solution at room temperature, adding alkali, stirring, standing and demixing, and then removing an aqueous layer; wherein the organic solvent is an aprotic solvent; the alkali is a hydroxide, carbonate or bicarbonate of an alkali metal or alkaline earth metal, or an amine mono- or polysubstituted by $C_1$-$C_6$ alkyl;

(2) drying an organic layer obtained over anhydrous magnesium sulfate and filtering; or subjecting an organic layer obtained directly to a next step without addition of anhydrous magnesium sulfate;

(3) adding acid halide or acid anhydride of a structural formula (IV) to the dried organic layer, stirring and concentrating; and (4) after concentrating to dryness to obtain an oily substance, adding an organic solvent, adding concentrated hydrochloric acid, and stirring to obtain ropinirole hydrochloride; wherein the organic solvent is an alcohol.

In the above step (1), after stirring, dissolving to obtain a clear solution and adding an alkali at room temperature, for example, further stirring for 20 min or more, and then standing and demixing. The volume of the organic solvent in milliliters may be 2 to 20 times, preferably 5 to 15 times, more preferably 8 to 12 times of the mass of ropinirole hydrochloride in grams. The volume of water in milliliters may be 5 to 20 times of the mass of ropinirole hydrochloride in grams. The molar amount of the alkali in step (1) is 1.5 to 25 times, preferably 5 to 15 times of the molar amount of ropinirole hydrochloride. Further, the organic solvent in step (1) may be dichloromethane, n-hexane, cyclohexane, ethyl acetate, isopropyl acetate, toluene, xylene or methyl tert-butyl ether. The alkali in step (1) may be selected from the group consisting of sodium carbonate, potassium hydroxide, sodium hydroxide, potassium carbonate, sodium bicarbonate, triethylamine and diisopropylamine.

In step (3), acid halide or acid anhydride is added to the organic layer, and the mixture is stirred for, for example, 10 min, and concentrated. The molar amount of the acid halide or acid anhydride may be 1 to 5 times of the molar amount of the ropinirole hydrochloride impurity A. The impurity-removing reagent, i.e., acid halide or acid anhydride, may be selected from the group consisting of acetyl chloride, propionyl chloride, benzoyl chloride, acetic anhydride, benzoic anhydride, and the like; preferably acetyl chloride, benzoyl chloride or acetic anhydride. The molar amount of the acid halide or acid anhydride is 1 to 5 times of the molar amount of the ropinirole hydrochloride impurity A.

In step (4), after adding concentrated hydrochloric acid and stirring, the reaction liquid can be cooled, centrifugal filtered and dried to obtain ropinirole hydrochloride. In step (4), after concentrating the organic layer to dryness to obtain an oily substance, a certain amount of an organic solvent is added to the obtained oily substance. The volume of the solvent in milliliters may be 2 to 20 times of the weight of the ropinirole hydrochloride in grams. The temperature of the reaction solution is maintained at 15±5° C. and a certain amount of concentrated hydrochloric acid is slowly added. The amount of concentrated hydrochloric acid may be 2 to 10 times, preferably 2 to 5 times of the molar amount of ropinirole hydrochloride. Stirring is continued for, for example, 30 min. The reaction liquid can be cooled to 5±5° C., stirred for 40 min, centrifugal filtered and dried to obtain ropinirole hydrochloride. Among which, the mass concentration of concentrated hydrochloric acid was 37%, which was calculated based on the amount of HCl in concentrated hydrochloric acid. The organic solvent in step (4) may be methanol, ethanol, isopropanol or n-butanol.

Nitrogen protection is strictly required in all of the above steps.

According to the method of the present invention, the impurity A in ropinirole hydrochloride can be effectively removed, and ropinirole hydrochloride can be obtained with a high yield and a high purity, so that the impurity A is controlled and the purity of the product reaches a medicinal standard.

DETAILED DESCRIPTION OF THE INVENTION

The following examples are intended to illustrate the invention in detail and not to limit the invention.

Nitrogen protection is required for the all process, which will not be repeated hereinafter.

Example 1

4-(2-di-n-propylaminoethyl)-1,3-dihydro-2H-indol-2-one hydrochloride (ropinirole hydrochloride, structural formula II) (8.9 g, 0.03 mol), 90 ml dichloromethane and 135 ml purified water were stirred in a 250 ml flask, meanwhile sodium hydroxide (6 g, 0.15 mol) was slowly added. After addition, the mixture was stirred for 20 min, and allowed to stand and demix. The aqueous layer was removed, and the organic layer was dried over 3 g anhydrous magnesium sulfate, stirred for 30 min, filtered and separated.

To the organic layer, acetyl chloride was added in an amount of 2 times of the molar amount of ropinirole hydrochloride impurity A, stirred for 10 min, and concentrated to dryness to obtain an oily substance.

125 ml isopropyl alcohol was added to the obtained oily substance, with the temperature of the reaction liquid maintained at 15±5° C., 9.0 g concentrated hydrochloric acid (with a mass concentration of 37%) was slowly added. After addition, the mixture was stirred for 30 min. Finally, the reaction liquid was cooled to 5±5° C., further stirred for 1 h, and centrifugal filtered to dryness.

Crude ropinirole hydrochloride was obtained after drying, in a yield of 90%. The purity detected by HPLC was 99.89%, and the content of impurity A was not detected (N.D.).

The HPLC analysis method of related substances of ropinirole hydrochloride is as follows:
Instrument: High performance liquid chromatograph equipped with UV detector
Column: Waters Xterra™ RP18250×4.6 mm, 5 μm
Mobile phase A: 2.84 g $Na_2HPO_4$ dissolved in 1000 ml water and adjusted to pH 11.0 with 1 mol/L NaOH
Mobile phase B: acetonitrile
Diluent: Mobile phase A:Mobile phase B=70:30 (% V/V)
Column temperature: 25° C. Detection wavelength: 250 nm
Flow rate: 1.0 ml/min Run time: 35 min
Injection volume: 20 μL
Gradient table:

| Time (min) | Mobile phase A (%V/V) | Mobile phase B (%V/V) |
| --- | --- | --- |
| 0 → 7.5 | 72 | 28 |
| 1.5 → 13 | 72 → 52 | 28 → 48 |
| 13 → 20 | 52 | 48 |
| 20 → 28 | 52 → 72 | 48 → 28 |
| 28 → 35 | 72 | 28 |

50 mg standard ropinirole hydrochloride was precisely weighed in a 100 ml volumetric flask, dissolved and diluted to the scale with a diluent, and mixed (the concentration of ropinirole hydrochloride is 500 μg/ml).

Example 2

4-(2-di-n-propylaminoethyl)-1,3-dihydro-2H-indol-2-one hydrochloride (ropinirole hydrochloride, structural formula II) (8.9 g, 0.03 mol), 90 ml n-hexane and 135 ml purified water were stirred in a 250 ml flask, meanwhile 8.4 g potassium hydroxide was slowly added. After addition, the mixture was stirred for 20 min, and allowed to stand and demix. The aqueous layer was removed.

To the organic layer, acetic anhydride was added in an amount of 2 times of the molar amount of ropinirole hydrochloride impurity A, stirred for 10 min, and concentrated to dryness to obtain an oily substance.

125 ml ethanol was added to the obtained oily substance, with the temperature of the reaction liquid maintained at 15±5° C., 9.0 g concentrated hydrochloric acid was slowly added. After addition, the mixture was stirred for 30 min. Finally, the reaction liquid was cooled to 5±5° C., further stirred for 1 h, and centrifugal filtered to dryness.

Crude ropinirole hydrochloride was obtained after drying, in a yield of 88%. The purity detected by HPLC was 99.91%, and the content of impurity A was 0.02%.

Example 3

4-(2-di-n-propylaminoethyl)-1,3-dihydro-2H-indol-2-one hydrochloride (ropinirole hydrochloride, structural formula II) (8.9 g, 0.03 mol), 90 ml ethyl acetate and 135 ml purified water were stirred in a 250 ml flask, meanwhile 15.9 g sodium carbonate was slowly added. After addition, the mixture was stirred for 20 min, and allowed to stand and demix. The aqueous layer was removed, and the organic layer was dried over 3 g anhydrous magnesium sulfate, stirred for 30 min, filtered and separated.

To the organic layer, propionyl chloride was added in an amount of 2 times of the molar amount of ropinirole hydrochloride impurity A, stirred for 10 min, and concentrated to dryness to obtain an oily substance.

125 ml methanol was added to the obtained oily substance, with the temperature of the reaction liquid maintained at 15±5° C., 9.0 g concentrated hydrochloric acid was slowly added. After addition, the mixture was stirred for 30 min. Finally, the reaction liquid was cooled to 5±5° C., further stirred for 1 h, and centrifugal filtered to dryness.

Crude ropinirole hydrochloride was obtained after drying, in a yield of 85%. The purity detected by HPLC was 99.88%, and the content of impurity A was 0.01%.

Example 4

4-(2-di-n-propylaminoethyl)-1,3-dihydro-2H-indol-2-one hydrochloride (ropinirole hydrochloride, structural formula II) (8.9 g, 0.03 mol), 90 ml toluene and 135 ml purified water were stirred in a 250 ml flask, meanwhile 20.7 g potassium carbonate was slowly added. After addition, the mixture was stirred for 20 min, and allowed to stand and demix. The aqueous layer was removed, and the organic layer was dried over 3 g anhydrous magnesium sulfate, stirred for 30 min, filtered and separated.

To the organic layer, benzoyl chloride was added in an amount of 2 times of the molar amount of ropinirole hydrochloride impurity A, stirred for 10 min, and concentrated to dryness to obtain an oily substance.

125 ml isopropanol was added to the obtained oily substance, with the temperature of the reaction liquid maintained at 15±5° C., 9.0 g concentrated hydrochloric acid was slowly added. After addition, the mixture was stirred for 30 min. Finally, the reaction liquid was cooled to 5±5° C., further stirred for 1 h, and centrifugal filtered to dryness.

Crude ropinirole hydrochloride was obtained after drying, in a yield of 90%. The purity detected by HPLC was 99.94%, and the content of impurity A was not detected (N.D.).

Example 5

4-(2-di-n-propylaminoethyl)-1,3-dihydro-2H-indol-2-one hydrochloride (ropinirole hydrochloride, structural formula II) (8.9 g, 0.03 mol), 90 ml toluene and 135 ml purified water were stirred in a 250 ml flask, meanwhile 20.7 g potassium carbonate was slowly added. After addition, the mixture was stirred for 20 min, and allowed to stand and demix. The aqueous layer was removed, and the organic layer was dried over 3 g anhydrous magnesium sulfate, stirred for 30 min, filtered and separated.

To the organic layer, benzoyl chloride was added in an amount of 1 time of the molar amount of ropinirole hydrochloride impurity A, stirred for 10 min, and concentrated to dryness to obtain an oily substance.

125 ml isopropanol was added to the obtained oily substance, with the temperature of the reaction liquid maintained at 15±5° C., 12.0 g concentrated hydrochloric acid was slowly added. After addition, the mixture was stirred for 30 min. Finally, the reaction liquid was cooled to 5±5° C., further stirred for 1 h, and centrifugal filtered to dryness.

Crude ropinirole hydrochloride was obtained after drying, in a yield of 90%. The purity detected by HPLC was 99.93%, and the content of impurity A was 0.03%.

Example 6

4-(2-di-n-propylaminoethyl)-1,3-dihydro-2H-indol-2-one hydrochloride (ropinirole hydrochloride, structural formula II) (8.9 g, 0.03 mol), 90 ml toluene and 135 ml purified water were stirred in a 250 ml flask, meanwhile 20.7 g potassium carbonate was slowly added. After addition, the mixture was stirred for 20 min, and allowed to stand and demix. The aqueous layer was removed, and the organic layer was dried over 3 g anhydrous magnesium sulfate, stirred for 30 min, filtered and separated.

To the organic layer, benzoyl chloride was added in an amount of 5 times of the molar amount of ropinirole hydrochloride impurity A, stirred for 10 min, and concentrated to dryness to obtain an oily substance.

125 ml isopropanol was added to the obtained oily substance, with the temperature of the reaction liquid maintained at 15±5° C., 6.0 g concentrated hydrochloric acid was slowly added. After addition, the mixture was stirred for 30 min. Finally, the reaction liquid was cooled to 5±5° C., stirred for 1 h, and centrifugal filtered to dryness.

Crude ropinirole hydrochloride was obtained after drying, in a yield of 91%. The purity detected by HPLC was 99.95%, and the content of impurity A was 0.01%.

The following table is a comparison table showing purities after purification for ropinirole hydrochloride with different contents of impurity A (monopropyl ropinirole).

|  | Purity before purification detected by HPLC | Impurity A content before purification by HPLC | Purity after purification detected by HPLC | Impurity A content after purification by HPLC |
| --- | --- | --- | --- | --- |
| Example 1 | 99.22% | 0.35% | 99.89% | N.D |
| Example 2 | 99.04% | 0.65% | 99.91% | 0.02% |
| Example 3 | 98.22% | 1.35% | 99.88% | 0.01% |
| Example 4 | 98.07% | 1.12% | 99.94% | N.D |
| Example 5 | 98.89% | 0.72% | 99.93% | 0.03% |
| Example 6 | 98.45% | 1.21% | 99.95% | 0.01% |

The invention claimed is:

1. A method for purifying ropinirole hydrochloride, 4-(2-di-n-propylaminoethyl)-1,3-dihydro-2H-indol-2-one hydrochloride, represented by a structural formula (II), comprising the following steps:

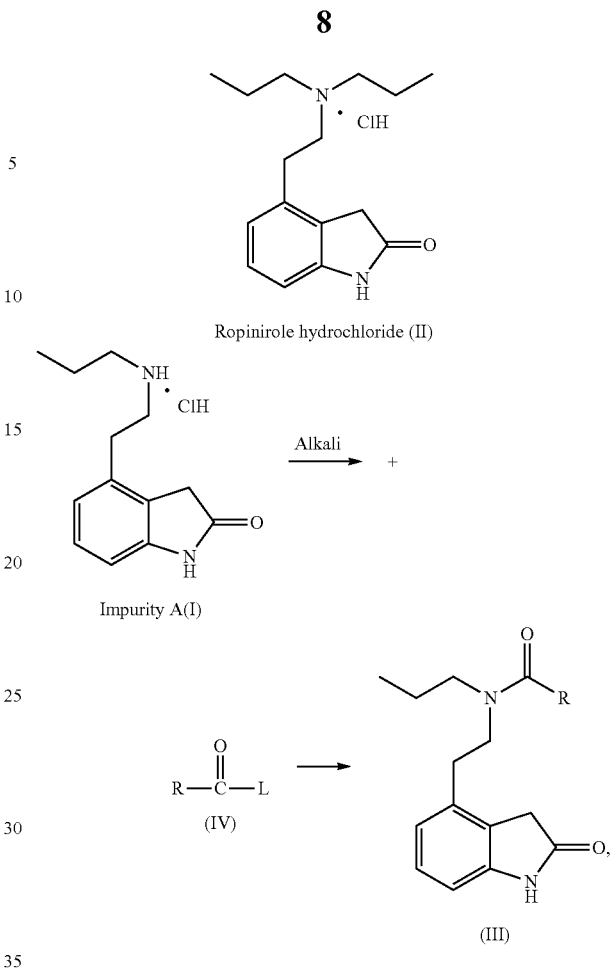

wherein —R represents $C_1$-$C_6$ alkyl or $C_6$-$C_{10}$ aromatic group;
-L represents halogen —X, or acyloxy $$-OCR;$$
$$\parallel$$
$$O$$

(1) mixing ropinirole hydrochloride containing an impurity A, monopropyl ropinirole, represented by a structural formula (I) with water and an organic solvent, stirring and dissolving to obtain a clear solution at room temperature, adding an alkali, stirring, standing for demixing, and removing an aqueous layer, wherein the organic solvent is an aprotic solvent; and the alkali is a hydroxide, carbonate or bicarbonate of an alkali metal or alkaline earth metal, or an amine mono- or polysubstituted by $C_1$-$C_6$ alkyl;

(2) drying an organic layer obtained over anhydrous magnesium sulfate and filtering; or subjecting the organic layer obtained directly to a next step without addition of anhydrous magnesium sulfate;

(3) adding acid halide or acid anhydride of a structural formula (IV) to the dried organic layer, stirring and concentrating; and (4) after concentrating to dryness to obtain an oily substance, adding an organic solvent to the obtained oily substance, adding a concentrated hydrochloric acid, and stirring to obtain ropinirole hydrochloride, wherein the organic solvent is an alcohol.

2. The method according to claim 1, wherein in step (1) the volume of the organic solvent in milliliters is 2 to 20 times of the mass of ropinirole hydrochloride in grams, and the volume of water in milliliters is 5 to 20 times of the mass of ropinirole hydrochloride in grams.

3. The method according to claim 1, wherein the molar amount of the alkali in step (1) is 1.5 to 25 times of the molar amount of ropinirole hydrochloride.

4. The method according to claim 1, wherein the organic solvent in step (1) is dichloromethane, n-hexane, cyclohexane, ethyl acetate, isopropyl acetate, toluene, xylene or methyl tert-butyl ether.

5. The method according to claim 1, wherein the alkali in step (1) is selected from the group consisting of sodium carbonate, potassium hydroxide, sodium hydroxide, potassium carbonate, sodium bicarbonate, triethylamine and diisopropylamine.

6. The method according to claim 1, wherein the acid halide or acid anhydride in step (3) is selected from the group consisting of acetyl chloride, propionyl chloride, benzoyl chloride, acetic anhydride and benzoic anhydride, and the molar amount of the acid halide or acid anhydride is 1 to 5 times of the molar amount of impurity A.

7. The method according to claim 6, wherein the acid halide or acid anhydride is selected from the group consisting of acetyl chloride, benzoyl chloride and acetic anhydride.

8. The method according to claim 1, wherein the volume of the organic solvent in milliliters in step (4) is 2 to 20 times of the mass of ropinirole hydrochloride in grams.

9. The method according to claim 1, wherein the molar amount of the concentrated hydrochloric acid in step (4) is 2 to 10 times of the molar amount of ropinirole hydrochloride.

10. The method according to claim 1, wherein the organic solvent in step (4) is methanol, ethanol, isopropanol or n-butanol.

11. The method according to claim 2, wherein the acid halide or acid anhydride in step (3) is selected from the group consisting of acetyl chloride, propionyl chloride, benzoyl chloride, acetic anhydride and benzoic anhydride, and the molar amount of the acid halide or acid anhydride is 1 to 5 times of the molar amount of impurity A.

12. The method according to claim 3, wherein the acid halide or acid anhydride in step (3) is selected from the group consisting of acetyl chloride, propionyl chloride, benzoyl chloride, acetic anhydride and benzoic anhydride, and the molar amount of the acid halide or acid anhydride is 1 to 5 times of the molar amount of impurity A.

13. The method according to claim 11, wherein the acid halide or acid anhydride is selected from the group consisting of acetyl chloride, benzoyl chloride and acetic anhydride.

14. The method according to claim 12, wherein the acid halide or acid anhydride is selected from the group consisting of acetyl chloride, benzoyl chloride and acetic anhydride.

15. The method according to claim 2, wherein the volume of the organic solvent in milliliters in step (4) is 2 to 20 times of the mass of ropinirole hydrochloride in grams.

16. The method according to claim 3, wherein the volume of the organic solvent in milliliters in step (4) is 2 to 20 times of the mass of ropinirole hydrochloride in grams.

17. The method according to claim 2, wherein the molar amount of the concentrated hydrochloric acid in step (4) is 2 to 10 times of the molar amount of ropinirole hydrochloride.

18. The method according to claim 3, wherein the molar amount of the concentrated hydrochloric acid in step (4) is 2 to 10 times of the molar amount of ropinirole hydrochloride.

19. The method according to claim 2, wherein the organic solvent in step (4) is methanol, ethanol, isopropanol or n-butanol.

20. The method according to claim 3, wherein the organic solvent in step (4) is methanol, ethanol, isopropanol or n-butanol.

* * * * *